United States Patent [19]

Agui et al.

[11] 3,954,775
[45] May 4, 1976

[54] THIAZOLO(5,4-F)QUINOLINE-8-CARBOXYLIC ACID DERIVATIVES

[75] Inventors: Hideo Agui, Toyonaka; Toru Mitani, Kyoto; Mitsuo Nakashita, Kobe; Eiichi Murayama, Takarazuka; Kousaku Okamura, Toyonaka; Takenari Nakagome, Nishinomiya; Toshiaki Komatsu, Takarazuka; Akio Izawa; Yasuko Eda, both of Toyonaka, all of Japan

[73] Assignee: Sumitomo Chemical Company, Limited, Osaka, Japan

[22] Filed: Oct. 17, 1974

[21] Appl. No.: 515,753

[30] Foreign Application Priority Data

| Oct. 17, 1973 | Japan | 48-117042 |
| Oct. 18, 1973 | Japan | 48-117496 |
| Nov. 22, 1973 | Japan | 48-131991 |
| Nov. 26, 1973 | Japan | 48-133175 |
| Dec. 13, 1973 | Japan | 48-140151 |
| Dec. 13, 1973 | Japan | 48-140152 |

[52] U.S. Cl. ............ 260/287 CF; 260/304 R; 424/258
[51] Int. Cl.² ............ C07D 513/04
[58] Field of Search ............ 260/287 AN, 287 CF, 260/283 S

[56] References Cited
UNITED STATES PATENTS

| 3,714,170 | 1/1973 | Dohmori et al. | 260/287 AN |
| 3,726,876 | 4/1973 | Dohmori et al. | 260/287 AN |
| 3,799,930 | 3/1974 | Nakagome et al. | 260/287 AN |

*Primary Examiner*—Alton D. Rollins
*Assistant Examiner*—David E. Wheeler
*Attorney, Agent, or Firm*—Sughrue, Rothwell, Mion, Zinn & Macpeak

[57] ABSTRACT

Thiazolo[5,4-f]quinoline-8-carboxylic acid derivatives having either the general formula (I):

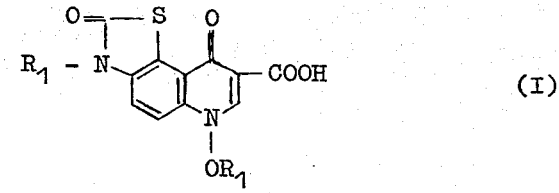

wherein $R_1$ is a lower alkyl group, a lower alkenyl group or a benzyl group; or the general formula (III-a):

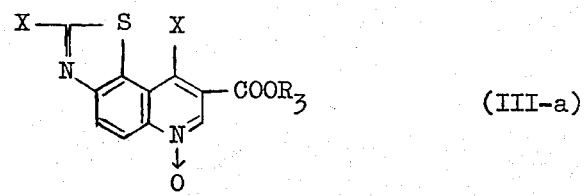

wherein $R_3$ is a lower alkyl group and X is a halogen atom; and methods for the preparation thereof. The compounds of the general formula (I) are useful as antibacterial agents against gram-negative and gram-positive bacteria. The compounds of the general formula (III-a) are useful as antifungal agents against eumycetes and also as an intermediate in a preparation of the compounds of the general formula (I).

4 Claims, No Drawings

THIAZOLO(5,4-F)QUINOLINE-8-CARBOXYLIC ACID DERIVATIVES

BACKGROUND OF THE INVENTION

1. FIELD OF THE INVENTION

This invention relates to antibacterial agents. More particularly, the invention relates to thiazolo [5,4-f]quinoline-8-carboxylic acid derivatives, which are useful as antibacterial agents; to intermediate useful in the preparation of the thiazolo-[5,4-f]-8-carboxylic acid derivatives; to processes for producing the thiazolo[5,4-f]-8-carboxylic acid derivatives; and to pharmaceutical compositions containing thiazolo[5,4-f]quinoline-8-carboxylic acid derivatives which are useful in the treatment of bacterial infections.

2. DESCRIPTION OF THE PRIOR ART

It is well known that various antibacterial agents have been developed, including nalidixic acid and 6-lower alkyl-2,3,6,9-tetrahydro-3-lower alkyl-2,9-dioxo-thiazolo[5,4-f]quinoline-8-carboxylic acids, but these compounds have some disadvantages. For example, although 6-ethyl-2,3,6,9-tetrahydro-3-methyl-2,9-dioxothiazolo[5,4-f]quinoline-8-carboxylic acid shows a noticeable antibacterial activity in vitro, it does not possess a sufficient antibacterial activity in vivo.

SUMMARY OF THE INVENTION

Accordingly, an object of this invention is to provide compounds which are useful as antibacterial agents overcoming the disadvantages of prior art antibacterial agents.

Another object of this invention is to provide compounds which are useful as antibacterial agents and also are useful as intermediates in the preparation of compounds useful as antibacterial agents.

A further object of this invention is to provide processes for producing antibacterial agents.

A still further object of this invention is to provide pharmaceutical compositions comprising a therapeutically effective amount of an antibacterial agent and a pharmaceutically acceptable carrier.

These and other objects of the invention will become apparent from the following detailed description of the invention.

As the result of research on compounds having a strong antibacterial activity in vivo as well as in vitro, it has been found that, among the various thiazolo[5,4-f]quinoline-8-carboxylic acid derivatives, the compounds having the general formula (I):

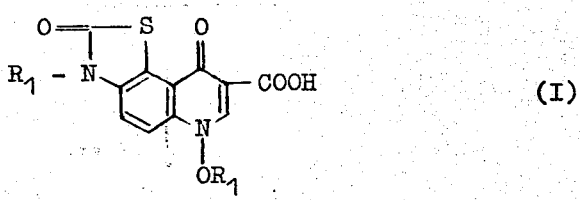

wherein $R_1$ is a lower alkyl group, a lower alkenyl group or a benzyl group; characteristically have excellent pharmacological properties such as strong antibacterial activity in vivo as well as in vitro, low toxicity, high serum level, and high urinary concentrations, and are useful in the treatment of bacterial infections, particularly urinary infections.

Also, in another embodiment of the invention, it has been found that a compound of the general formula (III-a)

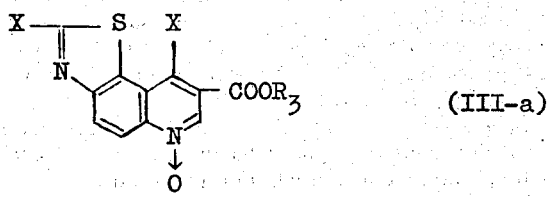

wherein $R_3$ is a lower alkyl group and X is a halogen atom has antifungal activity against eumycetes and is useful not only as an antifungal agent against eumycetes but also as an intermediate in the preparation of the compounds of the general formula (I).

DETAILED DESCRIPTION OF THE INVENTION

According to the invention, the compounds of the general formulae (I) and (III-a) can be prepared by a process as shown in the following reaction schematic:

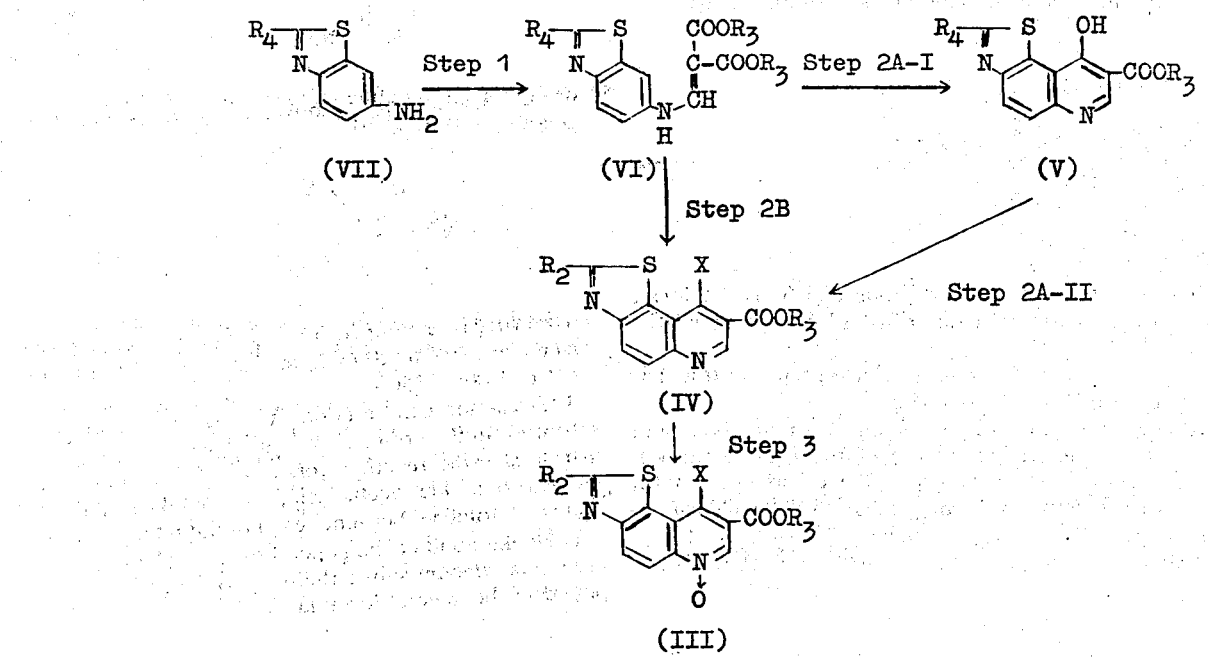

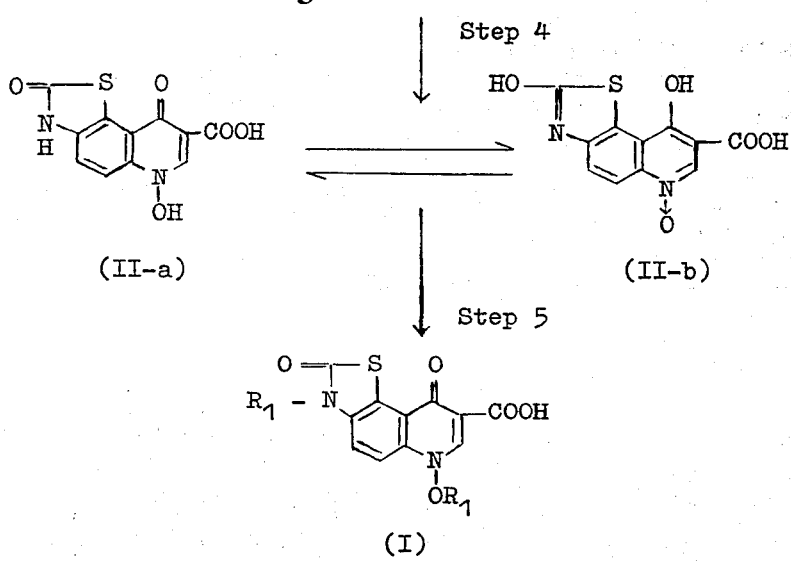

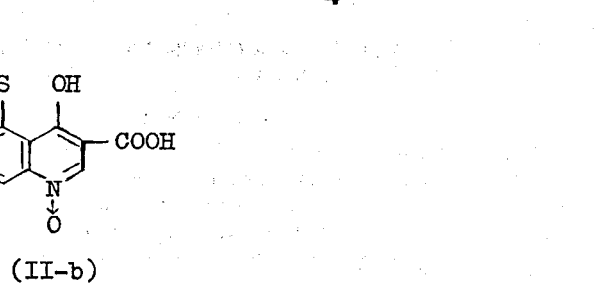

Step 4

Step 5

(I)

wherein $R_1$ is a lower alkyl group, a lower alkenyl group or a benzyl group; $R_2$ is a lower alkylsulfonyl group or a halogen atom; $R_3$ is a lower alkyl group; $R_4$ is a lower alkylsulfonyl group, a halogen atom or a hydroxy group; and X is a halogen atom.

The term "lower alkyl" as used herein designates a straight chain alkyl group having one to four carbon atoms (i.e., methyl, ethyl, n-propyl, n-butyl).

The term "lower alkenyl" as used herein designates a straight chain alkenyl group having two to four carbon atoms.

The term "halogen" as used herein designates a chlorine or a bromine atom.

The term "lower alkylsulfonyl" as used herein designates an alkylsulfonyl having 1 to 4 carbon atoms in the alkyl moiety thereof, for example, methylsulfonyl, ethylsulfonyl, propylsulfonyl, etc.

The above illustrated compounds of the general formulae (I), (II), (III), (IV), (V), (VI) and (VII) are novel and are not described in the literature or the patent art. The compound of the formula (V-a):

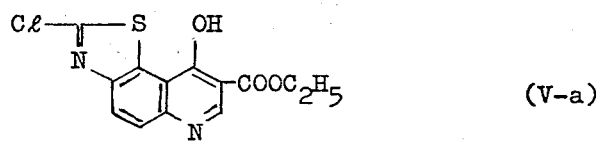

(i.e., where $R_3$ is an ethyl group and $R_4$ is a chlorine atom) is known and described in German Pat. No. 2,056,224.

The various steps described above are illustrated in greater detail in the following:

The compounds of the general formula (I) can be prepared using a compound of the general formula (VII) as a starting material. The compounds of the general formula (VII) are known compounds and described in J. Pharm. Soc. Japan, 71, 1442-4 (1951); Chemical Abstracts, 41, 754h; and U.S. Pat. No. 2,659,730.

Step 1: Preparation of the Compounds of the General Formula (VI):

The compounds of the general formula (VI)

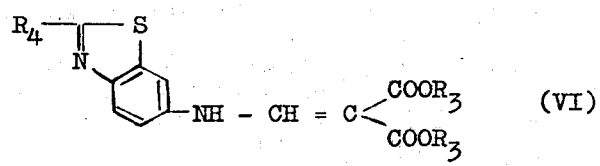

wherein $R_3$ is a lower alkyl group; and $R_4$ is a lower alkylsulfonyl group, a halogen atom or a hydroxy group; can be prepared by reacting a compound of the general formula (VII)

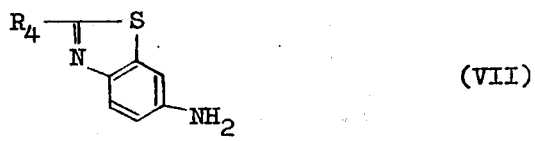

wherein $R_4$ is as defined above, with a compound of the general formula (VIII)

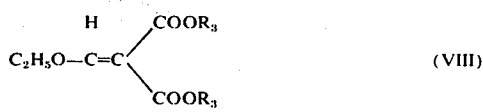

wherein $R_3$ is as defined above, at a temperature between about 60° to 200°C, preferably at a temperature between 100 to 150°C.

The reaction can be conducted in the absence of a solvent or in the presence of a suitable solvent which is inert under the reaction conditions, for example, dimethylformamide, acetic acid, an aromatic hydrocarbon (e.g., toluene, benzene, etc.) or a mixture thereof.

The compound of the general formula (VIII) can be used in an amount substantially equivalent to the compound of the general formula (VII).

When this reaction is conducted in a solvent, the concentration of the compound of the general formula (VII) in the solvent can range from about 5 to 100% gram per ml, preferably 10 to 50% gram per ml. The reaction period of time depends on the compound used, however it generally ranges from about 1 to 20 hours, more generally 2 to 10 hours. The reaction completion can be monitored by thin layer chromatographic analysis (Silicagel G: CHCl₃).

STEP 2: PREPARATION OF THE COMPOUNDS OF THE GENERAL FORMULA (V) (STEP 2A-I)

The compounds of the general formula (V)

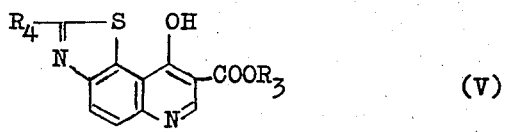

wherein R₃ is a lower alkyl group and R₄ is a lower alkylsulfonyl group, a halogen atom or a hydroxy group can be prepared by heating a compound of the general formula (VI) prepared as in Step 1 above in a suitable solvent at a temperature between about 150° to 300°C, preferably 240° to 280°C.

Suitable solvents which can be used in the reaction are any solvents which are inert to the compounds of the general formula (VI) under the reaction conditions employed and have a high boiling point. Suitable specific examples are, e.g., "Dowtherm" (a mixture of 26% by weight of diphenyl and 74% by weight of diphenyl ether), dibutylphthalate, diethylphthalate or diphenyl. Suitable concentrations of the compound of the general formula (V) in the solvent can range from about 2 to 20% gram per ml, preferably 4 to 15% gram per ml.

The reaction generally requires a reaction time of about 5 minutes to 2 hours.

STEP 2: PREPARATION OF THE COMPOUNDS OF THE GENERAL FORMULA (IV) (STEP 2A-II)

The compounds of the formula (IV)

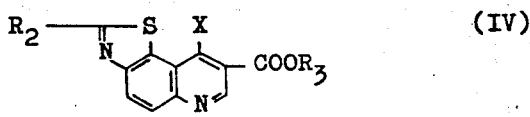

wherein R₂ is a lower alkylsulfonyl group or a halogen atom; and R₃ is a lower alkyl group; can be prepared by reacting a compound of the formula (V)

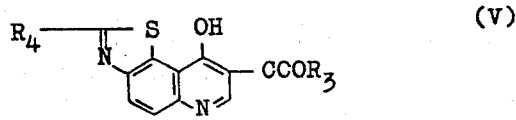

wherein R₃ and R₄ are as defined above, with a phosphorus halide (e.g., a phosphorus trihalide or a phosphorus pentahalide) or a phosphorus oxyhalide. Suitable examples of phosphorus halides and phosphorus oxyhalides which can be used in this step are phosphorus trichloride, phosphorus pentachloride and phosphorus oxychloride and these compounds are particularly preferred.

A preferred molar ratio of the phosphorus halide/oxyhalide to the compound of the general formula (VI) is about 1:1 to 50:1 with 2:1 to 15:1 being particularly preferred.

The reaction is carried out preferably at a temperature of from about 60° to 150°C using the phosphorus halide or phosphorus oxyhalide in an amount substantially equivalent to or in excess to, on an equivalent basis, the compound of the general formula (V).

The reaction can be carried out either in the absence of a solvent or in the presence of a suitable solvent which is inert under the reaction conditions. Suitable solvents include, for example, aromatic hydrocarbons (e.g., benzene, toluene, etc.), chloroform, dichloroethane and the like.

The concentration of the compound of the general formula (V) in the solvent can range from about 10 to 50% gram per ml. The reaction time is generally about 30 minutes to 20 hours, however, a preferred reaction time is 1 to 10 hours.

The completion of the reaction can be monitored by thin layer chromatographic analysis (Silicagel G: CHCl₃).

STEP 2: PREPARATION OF THE COMPOUNDS OF THE GENERAL FORMULA (IV) (STEP 2B)

The compounds (IV) can be prepared by reacting a compound of the general formula (VI)

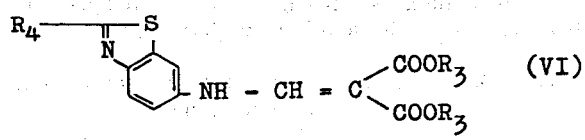

wherein R₃ is a lower alkyl group; and R₄ is a lower alkylsulfonyl group, a halogen atom or a hydroxy group; with a phosphorus halide or a phosphorus oxyhalide.

Suitable examples of phosphorus halides and phosphorus oxyhalides which can be used include phosphorus trihalides such as phosphorus trichloride, phosphorus pentahalides such as phosphorus pentachloride and phosphorus oxyhalides such as phosphorus oxychloride. A preferred molar ratio of the phosphorus halide/oxyhalide to the compound of the general formula (VI) is about 1:1 to 50:1, particularly 2:1 to 15:1.

The reaction can be carried out preferably by heating the compound of the general formula (VI) defined above with the phosphorus halide or phosphorus oxyhalide. A suitable reaction temperature ranges from about 30° to 200°C, preferably 60° to 150°C.

The reaction is generally carried out in the presence of a solvent inert under the reaction conditions, for example, in an aromatic hydrocarbon (e.g., benzene, toluene, etc.), chloroform and dichloroethane. It is, however, not essential that a solvent be used in this invention. When a solvent is used, a preferred concentration of the compound of the general formula (VI) in the solvent used is about 10 tp 50% gram per ml. The reaction time can range from about 1 to 50 hours, preferably 3 to 20 hours.

Step 3: Preparation of the Compounds of the General Formula (III)

The compounds of the general formula (III)

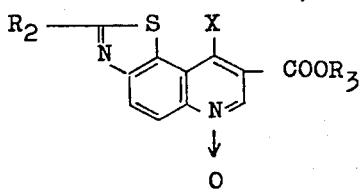

(III)

wherein $R_2$ is a lower alkylsulfonyl group or a halogen atom; $R_3$ is a lower alkyl group; and X is a halogen atom; can be prepared by reacting a compound of the general formula (IV)

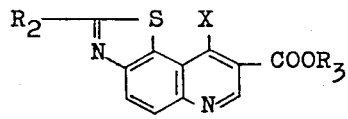

(IV)

wherein $R_2$, $R_3$ X are as defined above, with a peroxide.

Suitable peroxides which can be used in the reaction are aliphatic percarboxylic acids such as performic acid, peracetic acid, pertrifluoroacetic acid, monopermaleic acid, monopersuccinic acid, etc., aromatic percarboxylic acids such as perbenzoic acid, monoperphthalic acid, diperteraphthalic acid, m-chloroperbenzoic acid, etc., and inorganic peroxides such as hydrogen peroxide, etc. Of these peroxides, performic acid, peracetic acid, monopermaleic acid, perbenzoic acid, hydrogen peroxide and a mixture thereof are preferred, particularly monopermaleic acid.

The reaction is usually carried out at a temperature between about −50° to 150°C, preferably from −5° to 25°C.

The reaction can be carried out either in the absence of or in the presence of a suitable inert solvent, but preferably the reaction is carried out in the presence of an inert solvent such as diethyl ether, benzene, dichlorethane, chloroform or water, or in a parent acid or an anhydride of the peracid used, e.g., in acetic acid or in acetic anhydride when peracetic acid is used as the peroxide.

The peroxide is ordinarily used in an amount of substantially equivalent to or greater than, on an equivalency basis, the compound of the general formula (IV). However, the use of a large amount of the peroxide does not cause any serious difficulties in the reaction.

A preferred molar ratio of the peroxide to the compound of the general formula (IV) is about 1 : 1 to 20 : 1, preferably 1 : 1 to 10 : 1.

When a solvent is used, a preferred concentration of the compound of the general formula (IV) is about 1 to 20% gram per ml, preferably 2 to 10% gram per ml.

The reaction time is usually about 10 to 100 hours, preferably 15 to 50 hours.

Step 4: Preparation of 2,3,6,9-Tetrahydro-6-hydroxy-2,9-dioxothiazolo[5,4-f]quinoline-8-carboxylic Acid 2,3,6,9-Tetrahydro-6-hydroxy-2,9-dioxo-thiazolo[5,4-f]-quinoline-8-carboxylic acid can be prepared by hydrolyzing a compound of the general formula (III)

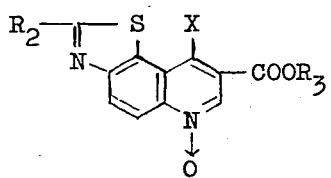

(III)

wherein $R_2$ is a lower alkylsulfonyl group or a halogen atom; $R_3$ is a lower alkyl group; and X is a halogen atom. This hydrolysis is carried out preferably using an acid such as hydrochloric acid, sulfuric acid, phosphoric acid or a mixture thereof, etc. or using a base such as sodium hydroxide, potassium carbonate, a sodium alkoxide, etc., in a suitable solvent such as water, methanol, acetic acid or a mixture thereof. The hydrolysis is carried out at a temperature from about room temperature to about 200°C, however, a most preferable temperature is from 50° to 150°C.

The molar ratios of the acid or the base used to the compound of the general formula (III) are usually about 4 : 1 to 100 : 1, preferably 5 : 1 to 50 : 1.

The concentration of the compound of the general formula (III) in the solvent can range from about 1 to 20% gram per ml, preferably 2 to 10% gram per ml.

The reaction time is generally about 1 to 50 hours, preferably 1 to 10 hours.

Step 5: Preparation of the compounds of the General Formula (I)

The compounds of the general formula (I)

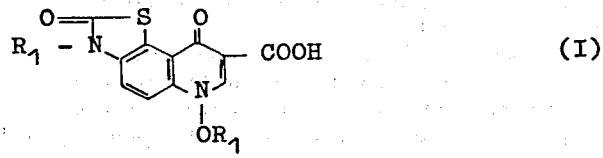

(I)

wherein $R_1$ is a lower alkyl group, a lower alkenyl group or a benzyl group; can be prepared by reacting 2,3,6,9-tetrahydro-6-hydroxy-2,9-dioxothiazolo[5,4-f]quinoline-8-carboxylic acid with a compound of the formula: $R_1X$, wherein $R_1$ and X are as defined above. In the case of the compounds of the general formula (I) wherein $R_1$ is a lower alkyl group, a dilower alkylsulfate of the formula: $(R_1O)_2SO_2$, wherein $R_1$ is a lower alkyl group can also be employed instead of the compound of the formula: $R_1X$.

Both the compound of the formula: $R_1X$ and the dilower alkylsulfate of the formula: $(R_1O)_2SO_2$ can be employed in an amount of about 3 to 20 times, preferably 3 to 10 times, on a molar equivalent basis to the compound of the general formula (I).

This reaction to prepare the compounds of the general formula (I) can be carried out either in the presence of or absence of a suitable solvent, but preferably is conducted in a solvent such as water, an alcohol (e.g., methanol, ethanol, etc.), acetone, toluene, dimethylformamide, dioxane, or a mixture thereof.

The reaction proceeds smoothly in the presence of an acid-acceptor. An acid-acceptor is a basic substance which preferably forms by-products which can be easily separated from the desired reaction product. Suitable examples of acid-acceptors include an alkali metal hydroxide (e.g., sodium hydroxide, potassium hydroxide, etc.), an alkali metal carbonate (e.g., sodium carbonate, potassium carbonate, etc.), an alkali metal bicarbonate (e.g., sodium bicarbonate, etc.), a sodium alkoxide (e.g., sodium methoxide, sodium ethoxide, etc.), sodium amide, sodium hydride and the like.

When a solvent is used, the concentration of the compound of the general formula (I) in the solvent is generally 2 to 20% gram per ml, preferably 5 to 10% gram per ml.

The reaction can be carried out at a temperature lower than about 200°C, but it is preferable to conduct the reaction at a temperature between 50 to 120°C, although it proceeds even at lower temperatures.

The molar ratio of the acid-acceptor to the compound of the general formula (I) is usually about 3 : 1 to 20 : 1, preferably 4 : 1 to 10 : 1.

The reaction time is usually about 5 to 50 hours, preferably 10 to 30 hours.

The compounds of the general formulae (I) and (III-a) generally are administered orally, for example, in the form of tablets, capsules, a powder, a solution, a suspension and the like, however, other methods and administration such as administration intraperitoneally, subcutaneously, intravenously, or intramuscularly can be employed if desired.

Compositions or preparations containing a compound of the general formula (I) or (III-a) as an active ingredient can be prepared by admixing a compound of the general formula (I) or the general formula (III-a) with one or more pharmaceutically acceptable carriers or diluents (e.g., cornstarch, gelatin, gum tragacanth, magnesium stearate, sucrose, lactose, etc.) and appropriately fabricating the compositions or preparations in the form of capsules, tablets, powders, syrups and the like using conventional methods well in the art.

Suitable oral dosages of the compound of the general formula (I) and the general formula (III-a) are usually about 100 to 1500 mg/day, preferably about 250 mg/day, for an adult (about 70 kg of body weight), administered in multiple doses 2 to 5 times daily. The above described compounds of the general formulae (I) and (III-a) can be administered in the free form or the compounds of the general formula (I) additionally in the form of the pharmaceutically acceptable salts thereof such as the alkali metal salts, e.g., the sodium and potassium salts.

Unless otherwise indicated in the evaluations and examples given hereinafter, all parts, percents, ratios and the like are by weight.

BIOLOGICAL ACTIVITY

The in vitro antibacterial activities were compared with 6-ethyl-2,3,6,9-tetrahydro-3-methyl-2,9-dioxothiazolo[5,4-f]quinoline-8-carboxylic acid (hereinafter Compound (D)) and nalidixic acid (hereinafter Compound (E)) using the tube dilution method.

These results obtained are shown in Table 1 below. 2,3,6,9-Tetrahydro-6-methoxy-3-methyl-2,9-dioxothiazolo[5,4-f]quinoline-8-carboxylic acid (hereinafter Compound (A)) and 2,3,6,9-tetrahydro-3-allyl-6-allyloxy-2,9-dioxothiazolo[5,4-f]quinoline-8-carboxylic acid (hereinafter Compound (C)) showed antibacterial activities on gram-negative bacteria, especially Compound (A) is as active as Compound (D) and more active than Compound (E) in vitro.

The antibacterial spectrum of 3-benzyl-6-benzyloxy-2,3,6,9-tetrahydro-2,9-dioxothiazolo[5,4-f]quinoline-8-carboxylic acid (hereinafter Compoud (B)) is different from the other compounds. Compound (B) exhibited inhibitory activity on gram-positive bacteria such as *Staphylococcus*, *Streptococcus*, *Diplococcus* and the others strains tested.

The results of in vivo studies of Compound (A) and Compound (D) are shown in Table 2. The mice were inoculated intraperitoneally with the test organisms in 5% gastric mucin. The test compounds were suspended in 0.5% carboxymethylcellulose and administered orally 1 hour and 6 hours after infection.

Compound (A) was more effective than Compound (D) in protecting mice against E. Coli No. 34 and P. Mirabilis GN 2425, but Compound (D) did not show activities on the organism tested.

Dry concentrations in serum of Compound (A) and Compound (D) were determined in the mice after a single oral dose of 50 mg/kg. The serum levels of Compound (A) reached a maximum within an hour. The peak value for Compound (A) was about 12 times higher than that of Compound (D).

Urinary excretions in fasting rats after a single oral dose of 50 mg/kg were also examined. Compound (A) was superior to Compound (D) in both recovery rate and urinary concentration.

Compound (A) was excreted in the urine about 7 times faster than Compound (D). Recovery rates of Compound (A) in the urine were 2.0% after 24 hours.

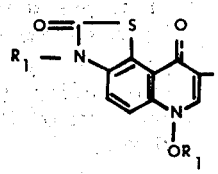

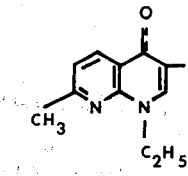

| Compound | R₁ | OR₁ |
|---|---|---|
| A | —CH₃ | —OCH₃ |
| B | —C₆H₅ | —OC₆H₅ |
| C | —CH₂CH=CH₂ | —OCH₂CH=CH₂ |
| D | —CH₃ | —C₂H₅ |
| E | | Nalidixic Acid |

Table 1

In vitro Antibacterial Activities on Laboratory Standard Strains

| Strain | Compound (mcg/ml) | | | | |
|---|---|---|---|---|---|
| | A | B | C | D | E |
| Escherichia coli NIHJ | 0.2 | >200 | 100 | 0.2 | 3.13 |
| Klebsiella pneumoniae PCI 602 | 0.2 | >200 | 200 | 0.2 | 3.13 |
| Proteus mirabilis GN-2425 | 0.39 | >200 | >200 | 0.78 | 6.25 |
| Proteus vulgaris HX-19 | 0.1 | >200 | 3.13 | 0.1 | 0.78 |
| Pseudomonas aeruginosa 104 | 25 | >200 | >200 | >200 | >200 |
| Staphylococcus aureus 209-P | 12.5 | 1.56 | 50 | 12.5 | 100 |
| Bacillus subtilis PCI 219 | 0.5 | 0.78 | | 0.25 | |
| Staphylococcus albus 1200 A | | 3.13 | | | |
| Streptococcus hemolyticus A-1 | | 1.56 | | | |
| Diplococcus pneumoniae Newfeld | | 1.56 | | | |
| Sarcina lutea PCI 1001 | | 1.56 | | | |

Table 2

In vivo Activity of Compound (A) and Compound (D)

| Test Organism | $ED_{50}$ (mg/kg) | |
|---|---|---|
| | Compound A | Compound D |
| Escherichia coli No. 34 | 50 | >100 |
| Escherichia coli No. 37 | >20 | >40 |
| Proteus mirabilis GN-2425 | 14 | >40 |

ANTIFUNGAL ACTIVITY

The activities of ethyl 2,9-dichlorothiazolo[5,4-*f*]quinoline-8-carboxylate-6-oxide (Compound (F)) on *Trichophyton rubrum* and *Aspergillus niger* were tested on Sabourand agar. Compound (F) exhibited inhibitory activity on the fungi tested. The minimum inhibitory concentrations were 0.78 mcg/ml for *Trichophyton rubrum* and 25 mcg/ml for *Aspergillus niger*. Compound (F) was found to be twice as active than griseofulvin in vitro.

TOXICITY

Preliminary Toxicological Data of Compound A in Rats

To 6-week old female rats of Spraugue-Dewlty-SLC strain, 1000 to 2000 mg/kg/day of Compound A were administered orally for 9 days. At all doses the body weight-gain slightly decreased but the body weight did not decrease. No significant symptoms were observed. In urinalysis with respect to pH, protein, glucose, ketone bodies and occult blood, no abnormality was found. Furthermore, no abnormal findings were observed in macroscopic examinations.

The following examples are given to illustrate the invention more specifically but the invention is not in any way to be construed as being limited to these examples.

EXAMPLE 1

Preparation of 2-Methylsulfonyl-6-[bis(2',2'-ethoxycarbonyl)ethenylamino]benzothiazole — Step 1

A mixture of 2.28 g of 6-amino-2-methylsulfonylbenzothiazole, 2.16 g of diethyl ethoxymethylenemalonate and 30 ml of dimethylformamide was heated at 100° – 110°C for 2 hours.

Removal of solvent and recrystallization from dimethylformamide gave 3.2 g of 2-methylsulfonyl-6-[bis(2',2'-ethoxycarbonyl)ethenylamino]benzothiazole as pale yellow prisms having a melting point of 183° – 184°C.

Elemental Analysis

Calculated for: $C_{16}H_{18}N_2O_6S_2$. C: 48.23%; H: 4.55%; N: 7.03%. Found: C: 48.10%; H: 4.13%; N: 7.22%.

EXAMPLE 2

Preparation of 2-Hydroxy-6-[bis(2',2'-ethoxycarbonyl)ethenylamino]benzothiazole — Step 1

A mixture of 1.66 g of 6-amino-2-hydroxybenzothiazole, 2.16 g of diethyl ethoxymethylenemalonate and 30 ml of dimethylformamide was heated at 120°C for 1 hour.

Removal of solvent and recrystallization from a mixture of dimethylformamide and methanol gave 2.69 g of 2-hydroxy-6-[bis-(2',2'-ethoxycarbonyl)ethenylamino]benzothiazole as yellow prisms having a melting point of 218° – 219°C. (Yield: 80%)

Elemental Analysis

Calculated for $C_{15}H_{16}N_2O_5S$. C: 49.22%; H: 4.41%; N: 3.83%. Found: C: 48.93%; H: 4.32%; N: 3.95%.

EXAMPLE 3

Preparation of Ethyl 9-Hydroxy-2-methylsulfonylthiazolo[5,4-*f*]quinoline-8-carboxylate — Step 2A-I To 60 ml of Dowtherm A heated to 250° – 257°C was added 3.98 g of 2-methylsulfonyl-6-[bis(2',2'-ethoxycarbonylethenylamino]benzothiazole and the mixture was stirred for 13 minutes while the reaction temperature was kept at 250° – 257°C. Then, the reaction mixture was allowed to cool.

The precipitated brown-yellow crystals were collected by filtration, washed with ethanol and dried to give 3.43 g of ethyl 9-hydroxy-2-methylsulfonylthiazolo[5,4-*f*]quinoline-8-carboxylate having a melting point of 318° – 320°C (decomposition). (Yield: 97.5%)

Elemental Analysis

Calculated for: $C_{14}H_{12}N_2S_2O_5$. C: 47.72%; H: 3.43%; N: 7.95%. Found: C: 47.34%; H: 3.56%; N: 7.98.

EXAMPLE 4

Preparation of Ethyl 2-Chloro-9-hydroxythiazolo[5,4-*f*]quinoline-8-carboxylate — Step 2A-I To 100 ml of Dowtherm A heated to 250° – 255°C was added 5.0 g of 2-chloro-6-[bis(2',2'-ethoxycarbonyl)ethenylamino]benzothiazole and then the mixture was stirred for 15 minutes, while the temperature was kept at 250° – 255°C.

After cooling, the precipitated crystals were collected by filtration, washed with ethanol and dried under reduced pressure to give 4.0 g of ethyl 2-chloro-9-hydroxythiazolo[5,4-f]quinoline-8-carboxylate as yellow crystals having a melting point above 300°C. (Yield: 92%)

EXAMPLE 5

Preparation of Ethyl 2,9-Dichlorothiazolo[5,4-f]quinoline-8-carboxylate — Step 2A-II A mixture of 20 g of ethyl 2-chloro-9-hydroxythiazolo[5,4-f]quinoline-8-carboxylate and 200 ml of phosphorus oxychloride was refluxed for 3 hours. The reaction mixture was concentrated to a small volume under reduced pressure and the residue was poured into ice-water, neutralized with an aqueous sodium carbonate solution and extracted with chloroform. The chloroform layer was wahsed with water and concentrated to dryness under reduced pressure.

The residue was washed with ethylacetate to give 7.02 g of ethyl 2,9-dichlorothiazolo[5,4-f]quinoline-8-carboxylate as a yellow powder having a melting point of 143° – 146°C.

Elemental Analysis

Calculated for: $C_{13}H_8Cl_2N_2O_2S$. C: 47.7%; H: 2.45%; N: 8.56%. Found: C: 47.80%; H: 2.40%; N: 8.62%.

EXAMPLE 6

Preparation of Ethyl 9-Chloro-2-methylsulfonylthiazolo[5,4-f]quinoline-8-carboxylate — Step 2A-II A mixture of 3.52 g of ethyl 9-hydroxy-2-methylsulfonylthiazolo[5,4-f]quinoline-8-carboxylate and 30 ml of phosphorus oxychloride was refluxed for 6 hours.

After removal of excess phosphorus oxychloride under reduced pressure, the residue was added to ice-water, neutralized with an aqueous sodium carbonate solution and extracted with chloroform. The chloroform layer was washed with water and concentrated under reduced pressure to give 3.6 g of pale yellow crystals having a melting point of 176° – 178°C.

Recrystallization from a mixture of chloroform and methanol gave pale yellow prisms having a melting point of 178° – 179°C.

Elemental Analysis

Calculated for: $C_{14}H_{11}ClN_2O_4S_2$. C: 45.38%; H: 2.99%; N: 7.56%. Found: C: 45.39%; H: 2.98%; N: 7.53%.

EXAMPLE 7

Preparation of Ethyl 2,9-Dichlorothiazolo[5,4-f]quinoline-8-carboxylate — Step 2A-II A mixture of 3.0 g of ethyl 2-chloro-9-hydroxythiazolo[5,4-f]quinoline-8-carboxylate, 20 ml of phosphorus oxychloride and 300 ml of dichloroethane was refluxed for 8 hours.

The resulting reaction mixture was treated in the same manner as described in Example 5 to give ethyl 2,9-dichlorothiazolo[5,4-f]quinoline-8-carboxylate.

EXAMPLE 8

Preparation of Ethyl 2,9-Dichlorothiazolo[5,4-f]quinoline-8-carboxylate — Step 2A-II A mixture of 3.09 g of ethyl 2-chloro-9-hydroxythiazolo[5,4-f]quinoline-8-carboxylate, 20 ml of phosphorus oxychloride and 1.0 g of phosphorus trichloride was refluxed for 1.5 hours.

The reaction mixture was treated in the same manner as described in Example 5 to give ethyl 2,9-dichlorothiazolo[5,4-f]quinoline-8-carboxylate.

EXAMPLE 9

Preparation of Ethyl 2,9-Dichlorothiazolo[5,4-f]quinoline-8-carboxylate — Step 2A-II A mixture of 3.09 g of ethyl 2-chloro-9-hydroxythiazolo[5,4-f]quinoline-8-carboxylate, 20 ml of phosphorus oxychloride and 0.2 g of phosphorus pentachloride was refluxed for 1 hour and the reaction mixture was treated in the same manner as described in Example 5 to give ethyl 2,9-dichlorothiazolo[5,4-f]quinoline8-carboxylate.

EXAMPLE 10

Preparation of Ethyl 2,9-Dichlorothiazolo[5,4-f]quinoline-8-carboxylate — Step 2B A mixture of 5.5 g of 2-chloro-6-[bis(2′,2′-ethoxycarbonyl)ethenylamino]benzothiazole and 150 ml of phosphorus oxychloride was refluxed for 12 hours. The reaction mixture was concentrated to a small volume under reduced pressure.

The residue was poured into ice-water, neutralized with an aqueous sodium carbonate solution and extracted with chloroform. The chloroform layer was washed with water and concentrated to dryness under reduced pressure.

This crude product obtained was recrystallized from ethyl acetate to give 4.0 g of ethyl 2,9-dichlorothiazolo[5,4-f]quinoline-8-carboxylate as a pale yellow powder.

EXAMPLE 11

Preparation of Ethyl 2,9-Dichlorothiazolo[5,4-f]quinoline-8-carboxylate — Step 2B A mixture of 3.55 g of 2-chloro-6-[bis(2′,2′-ethoxycarbonyl)ethenylamino]benzothiazole, 50 ml of phosphorus oxychloride and 100 ml of toluene was refluxed for 12 hours.

The resulting mixture was treated in the same manner as described in Example 10 to give 2.45 g of ethyl 2,9-dichlorothiazolo[5,4-f]quinoline-8-carboxylate. (Yield: 75%)

EXAMPLE 12

Preparation of Ethyl 2,9-Dichlorothiazolo[5,4-f]quinoline-8-carboxylate — Step 2B A mixture of 3.55 g of 2-chloro-6-[bis(2′,2′-ethoxycarbonyl)ethenylamino]benzothiazole, 1.38 g of phosphorus trichloride and 50 ml of phosphorus oxychloride was refluxed for 10 hours.

The reaction mixture was treated in the same manner as described in Example 10 to give 2.32 g of ethyl 2,9-dichlorothiazolo[5,4-*f*]quinoline-8-carboxylate. (Yield: 71%)

EXAMPLE 13

Preparation of Ethyl 2,9-Dichlorothiazolo[5,4-*f*]quinoline-8-carboxylate - Step 2B A mixture of 3.55 g of 2-chloro-6-[bis(2',2'-ethoxycarbonyl)ethenylamino]benzoothiazole, 2.10 g of phosphorus pentachloride and 50 ml of phosphorus oxychloride was refluxed for 10 hours.

The resulting mixture was treated in the same manner as described in Example 10 to give 2.52 g of ethyl 2,9-dichlorothiazolo[5,4-*f*]quinoline-8-carboxylate. (Yield: 77%)

EXAMPLE 14

Preparation of Ethyl 2,9-Dichlorothiazolo[5,4-*f*]quinoline-8-carboxylate — Step 2B A mixture of 3.36 g of 2-hydroxy-6-[bis(2',2'-ethoxycarbonyl)ethenylamino]benzothiazole and 100 ml of phosphorus oxychloride was refluxed for 12 hours.

The resulting mixture was treated in the same manner as described in Example 10 to give 2.56 g of ethyl 2,9-dichlorothiazolo[5,4-*f*]quinoline-8-carboxylate. (Yield: 85%)

EXAMPLE 15

Preparation of Ethyl 2,9-Dichlorothiazolo[5,4-*f*]quinoline-8-carboxylate — Step 2B A mixture of 2 g of 2-methylsulfonyl-6-[bis(2',2'-ethoxycarbonyl)ethenylamino]benzothiazole and 40 ml of phosphorus oxychloride was refluxed for 14 hours.

The resulting mixture was treated in the same manner as described in Example 10 to give 1.5 g of ethyl 9-chloro-2-methylsulfonylthiazolo[5,4-*f*]quinoline-8-carboxylate.

Recrystallization from a mixture of chlorofrom and methanol gave pale yellow prisms having a melting point of 170°–179° C.

Elemental Analysis

Calculated for: $C_{14}H_{11}ClN_2O_4S_2$. C: 45.38%; H: 2.99%; N: 7.56%. Found: C: 45.39%; H: 2.98%; N: 7.53%.

EXAMPLE 16

Preparation of Ethyl 2,9-Dichlorothiazolo[5,4-*f*]quinoline-8-carboxylate-6-oxide — Step 3

A mixture of 1.0 g of ethyl 2,9-dichlorothiazolo[5,4-*f*]quinoline-8-carboxylate, 1.0 g of m-chloroperbenzoic acid and 80 ml of chloroform was stirred for 55 hours at 0° – 5° C and 20 ml of a 5% sodium carbonate aqueous solution was added thereto at 0° – 5° C. The resulting mixture was stirred for 30 minutes.

The chloroform was separated from the mixture, washed and concentrated to dryness under reduced pressure to give a yellow solid. The product thus obtained was washed with ethyl acetate to give 0.58 g of ethyl 2,9-dichlorothiazolo[5,4-*f*]quinoline-8carboxylate-6-oxide having a melting point of 198° – 199° C. (Yield: 55.4%)

Elemental Analysis

Calculated for: $C_{13}H_4Cl_2N_2O_3S$. C: 45.48%; H: 2.33%; N: 8.16%. Found: C: 45.47%; H: 2.27%; N: 8.19%.

EXAMPLE 17

Preparation of Ethyl 2,9-Dichlorothiazolo[5,4-*f*]quinoline-8-carboxylate-6-oxide — Step 3

A mixture of 4.5 g of maleic anhydride, 1.56 g of a 35% hydrogen peroxide aqueous solution and 80 ml of chloroform was stirred at 0° – 5° C for 30 minutes and 1.0 g of ethyl 2,9-dichlorothiazolo[5,4-*f*]quinoline-8-carboxylate was added thereto.

After the resulting mixture was stirred at 0° – 5° C for 48 hours, the chloroform layer was separated from the mixture, washed with a 5% sodium carbonate aqueous solution and water, and concentrated to dryness under reduced pressure to give a yellow solid. The product thus obtained was washed with ethyl acetate to give 0.90 g of pure ethyl 2,9-dichlorothiazolo[5,4-*f*]quinoline8-carboxylate-6-oxide. (Yield: 95%)

EXAMPLE 18

Preparation of Ethyl 9-Chloro-2-methylsulfonylthiazolo[5,4-f]quinoline-8-carboxylate-6-oxide — Step 3

A mixture of 5.4 g of maleic anhydride, 5.4 g of a 35% hydrogen peroxide aqueous solution and 200 ml of chloroform was stirred at 0° – 5° C for 30 minutes. To the resulting mixture was added 3.7 g of ethyl 9-chloro-2-methylsulfonylthiazolo[5,4-*f*]quinoline-8-carboxylate and the mixture was stirred at 0° – 5° C for 50 hours.

The reaction mixture thus obtained was treated in the same manner as described in Example 9 to give 2.78 g of ethyl 9-chloro2-methylsulfonylthiazolo[5,4-*f*]quinoline-8-carboxylate-6-oxide.

Recrystallization from a mixture of chloroform and ethyl acetate gave yellow prisms having a melting point of 222° C (decomposition).

Elemental Analysis

Calculated for: $C_{14}H_{11}ClN_2S_2O_5$. C: 43.50%; H: 2.87%; N: 7.25%. Found: C: 43.49%; H: 2.81%; N: 7.19%.

EXAMPLE 19

Preparation of 2,3,6,9-Tetrahydro-6-hydroxy-2,9-dioxothiazolo[5,4-*f*]quinoline-8-carboxylic Acid — Step 4

A mixture of 1.0 g of ethyl 2,9-dichlorothiazolo[5,4-*f*]quinoline-8-carboxylate-6-oxide and 20 ml of a 5% potassium hydroxide aqueous solution was refluxed for 7 hours.

After treating the mixture with charcoal, the reaction mixture was adjusted to a pH of 1 – 2 with adding conc-hydrochloric acid.

The white crystals precipitated were collected by filtration, washed, and dried to give 0.79 g of pure 2,3,6,9-tetrahydro-6-hydrox-2,9-dioxothiazolo[5,4-f]quinoline-8-carboxylic acid having a melting point above 300° C. (Yield: 97%)

Elemental Analysis

Calculated for: $C_{11}H_6N_2O_5S$. C: 47.48%; H: 2.16%; N: 10.07%. Found: C: 47.31%; H: 2.18%; N: 10.09%.

EXAMPLE 20

Preparation of 2,3,6,9-Tetrahydro-6-hydroxy-2,9-dioxothiazolo[5,4-f]quinoline-8-carboxylic Acid — Step 4

A mixture of ethyl 2,9-dichlorothiazolo[5,4-f]quinoline8-carboxylate-6-oxide (14.8g) and 350 ml of a 5% sodium hydroxide aqueous solution was refluxed for 5 hours.

The reaction mixture was treated in the same way as described in Example 19 to give 12.0 g of 2,3,6,9-tetrahydro-6-hydroxy-2,9-dioxothiazolo[5,4-f]quinoline-8-carboxylic acid. (Yield: 94%)

EXAMPLE 21

Preparation of Ethyl 2,9-Dichlorothiazolo[5,4-f]quinoline-8-carboxylate — Step 2B A mixture of 3.87 g of ethyl 9-chloro-2-methylsulfonylthiazolo[5,4-f]quinoline-8-carboxylate-6-oxide and 60 ml of a 5% sodium hydroxide aqueous solution was refluxed for 5 hours.

The resulting reaction mixture was treated in the same way as described in Example 5 to give 2.22 g of 2,3,6,9-tetrahydro-6-hydroxy-2,9-dioxothiazolo[5,4-f]quinoline-8-carboxylic acid. (Yield: 80%)

EXAMPLE 22

Preparation of 2,3,6,9-Tetrahydro-6-methoxy-3-methyl-2,9-dioxothiazolo[5,4-f]quinoline-8-carboxylic Acid —Step 5

A mixture of 1.0 g of 2,3,6,9-tetrahydro-6-hydroxy-2,9-dioxothiazolo[5,4-f]quinoline-8-carboxylic acid, 0.9 g of an 85% potassium hydroxide aqueous solution, 15 ml of water, 5 ml of methanol and 2.3 g of methyl iodide was stirred for 19 hours at room temperature (about 20°–30°C) and then 1 g of methyl iodide was added to the mixture. The resulting mixture was stirred at a temperature of about b 50°–60°C for 7 hours.

After the reaction was completed, the excess methyl iodide and the solvent were removed by distillation under reduced pressure. The residue was adjusted to a pH of 1 by adding conchydrochloric acid and then heated at 90°– 100°C for 1 hour with stirring.

After the resulting reaction mixture was cooled, 1.03 g of white crystals which had precipitated was collected by filtration and recrystallized from dimethylformamide to give pure 2,3,6,9-tetrahydro-6-methoxy-3-methyl-2,9-dioxothiazolo[5,4-f]-quinoline-8-carboxylic acid as colorless needles having a melting point above 300°c.

Elemental Analysis

Calculated for: $C_{13}H_{10}N_2O_5S$.
C: 50.98%; H: 3.27%; N: 9.15%; S: 10.46%.
Found: C: 51.04%; H: 3.28%; N: 9.07%; S: 10.56%.

EXAMPLE 23

Preparation of 2,3,6,9-Tetrahydro-6-methoxy-3-methyl-2,9-dioxothiazolo[5,4-f]quinoline-8-carboxylic Acid —Step 5

To a mixture of 1.0 g of 2,3,6,9-tetrahydro-6-hydroxy-2,9-dioxothiazolo[5,4-f]quinoline-8-carboxylic acid, 0.84 g of an 85% —potassium hydroxide aqueous solution and 15 ml of water was added dropwise 2.26 g of dimethylsulfate at 0°– 5°C over a 10 minute period. The resulting mixture was stirred at 30°– 35°C for 6 hours and additionally for 12 hours at room temperature.

After the reaction was completed, the reaction mixture was treated in the same manner as described in Example 22 to give pure 2,3,6,9-tetrahydro-6-methoxy-3-methyl-2,9-dioxothiazolo-[5,4-f]quinoline-8-carboxylic acid.

EXAMPLE 24

Preparation of 2,3,6,9-Tetrahydro-6-allyloxy-3-allyl-2,9-dioxothiazolo[5,4-f]quinoline-8-carboxylic Acid —Step 5

To a mixture of 1.0 g of 2,3,6,9-tetrahydro-6-hydroxy-2,9-dioxothiazolo[5,4-f]quinoline-8-carboxylic acid, 0.91 g of an 85% —potassium hydroxide aqueous solution, 20 ml of water and 7 ml of methanol was added dropwise 2.72 g of allyl iodide. The resulting mixture was stirred at room temperature for 22 hours and then heated at 50°– 60°C for 6.5 hours with stirring.

After removal ov the methanol by distillation, the residue was adjusted to a pH of 1 by adding 6N hydrochloric acid and the residue stirred for 1 hour to 90°– 100°C.

After cooling, 1.13 g of precipitated crystals was collected by filtration and the crystals were recrystallized from a mixture of dimethylformamide and water to give 0.5 g of pure 2,3,6,9-tertrahydro-6-allyloxy-3-allyl-2,9-dioxothiazolo[5,4-f]-quinoline-8-carboxylic acid as white needles having a melting point of 253°–255°C (decomposition). (Yield: 41.4%)

Elemental Analysis

Calculated for: $C_{17}H_{14}N_2O_5S$.
C. 56.98%; H: 3.91%; N: 7.82%; S: 8.94%.
Found: C: 56.86%; H: 4.08%; N: 7.93%; S: 9.29%.

EXAMPLE 25

Preparation of 2,3,6,9-Tetrahydro-6-benzyloxy-3-benzyl-2,9-dioxothiazolo[5,4-f]quinoline-8-carboxylic Acid — Step 5

To a mixture of 1.0 g of 2,3,6,9-tetrahydro-6-hydroxy-2,9-dioxothiazolo[5,4-f]quinoline-8-carboxylic acid, 0.96 g of an 85% — potassium hydroxide aqueous solution, 20 ml of water and 7 ml of methanol was added dropwise 2.77 g of benzyl bromide and the mixture was stirred for 44 hours at room temperature.

After removal of the methanol by distillation, the residue was adjusted to a pH of 1 by adding 6N hydrochloric acid and the mixture was heated at 90°– 100°C for 1 hour wiht stirring.

The resulting reaction mixture was cooled and the precipitated crystals were collected by filtration. The crude crystals obtained were recrystallized from a mixture of chloroform and methanol to give 0.42 g of 2,3,6,9-tetrahydro-6-benzyloxy-3-benzyl-2,9-dioxo-thiazolo[5,4-*f*]quinoline-8-carboxylic as white needles having a melting point of 245°– 246°C.

Elemental Analysis

Calculated for: $C_{25}H_{18}N_2O_5S$.
C: 65.50%; H: 3.93%; N: 6.11%; S: 6.99%.
Found: C: 64.92%; H: 4.02%; N: 5.88%; S: 6.53%.

While the invention has been described in detail and with reference to specific embodiments thereof, it will be apparent to one skilled in the art that various changes and modifications can be made theein without departing from the spirit and scope thereof.

What is claimed is:

1. A compound of the formula (I)

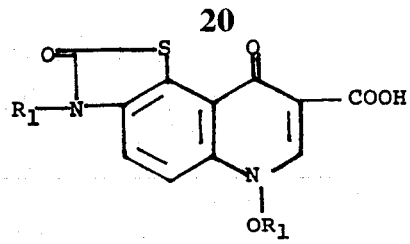

wherein $R_1$ is a straight chain $C_1$–$C_4$ alkyl group, a straight chain $C_2$–$C_4$ alkenyl group or a benzyl group, and the pharmaceutically acceptable salts thereof.

2. The compound of claim 1, wherein said compound is 2,3,6,9-tetrahydro-6-methoxy-3-methyl-2,9-dioxo-thiazolo[5,4-*f*]quinoline-8-carboxylic acid.

3. The compound of claim 1, wherein said compound is 2,3,6,9-tetrahydro-6-allyloxy-3-allyl-2,9-dioxo-thiazolo[5,4-*f*]quinoline-8-carboxylic acid.

4. The compound of claim 1, wherein said compound is 2,3,6,9-tetrahydro-6-benzyloxy-3-benzyl-2,9-dioxo-thiazolo[5,4-*f*]-quinoline-8-carboxylic acid.

* * * * *